US00PP11081P

United States Patent [19]

Oliver

[11] Patent Number: Plant 11,081

[45] Date of Patent: Oct. 5, 1999

[54] HEUCHERELLA PLANT NAMED 'QUICKSILVER'

[76] Inventor: Charles G. Oliver, R.D. 2, Box 110, Scottdale, Pa. 15683

[21] Appl. No.: 09/005,618

[22] Filed: Jan. 12, 1998

[51] Int. Cl.[6] ..... A01H 5/00

[52] U.S. Cl. ..... Plt./263

[58] Field of Search ..... Plt./263

*Primary Examiner*—Howard J. Locker
*Assistant Examiner*—Kent L. Bell
*Attorney, Agent, or Firm*—C. A. Whealy

[57] ABSTRACT

A distinct cultivar of Heucherella plant named 'Quicksilver', characterized by its proportional plants with respect to quantity of flowers to foliage density; unique bronze leaves with a silver metallic sheen most pronounced in the interveinal areas; pink flower buds; numerous fringed, bell-shaped white flowers contrasted by dark flowering stems; and excellent garden performance.

2 Drawing Sheets

The present invention relates to a new and distinct cultivar of Heucherella, botanically known as ×*Heucherella alba*, and hereinafter referred to by the cultivar name 'Quicksilver'. Heucherella is a genus that contains intergeneric hybrids between the genera Heuchera and Tiarella.

The new cultivar is a product of a planned breeding program conducted by the inventor in Scottdale, Pa. The objective of the breeding program is to create new garden-type Heucherella cultivars having good flower to foliage proportion; showy and attractive flowers; attractive foliage; and good garden performance.

The new cultivar was selected by the inventor from seedling progeny from a bigeneric cross made in 1993 by the inventor of the *Tiarella cordifolia* var. collina 'Montrose Selection' (not patented) as the male or pollen parent with the Heuchera sp. cultivar 'Quilter's Joy' (not patented) as the female or seed parent. The new cultivar was selected by the inventor at his nursery in Scottdale, Pa. from these seedlings.

Asexual reproduction of the new cultivar by divisions and by shoot cuttings taken at Scottdale, Pa., has shown that the unique features of this new Heucherella plant are stable and reproduced true to type in successive generations of asexual reproduction.

In side-by-side comparisons in Scottdale, Pa., under commerical practice, plants of the new Heucherella are different from plants of the male parent, the *Tiarella cordifolia* var. collina 'Montrose Selection' in the following characteristics:

1. Plants of the new Heucherella are larger and more showy than plants of the cultivar 'Montrose Selection'.

2. Leaves of plants of the new Heucherella are metallic bronze and silver whereas leaves of plants of the cultivar 'Montrose Selection' are green and maroon.

3 . Plants of the new Heucherella flower for a longer period of time than plants of the cultivar 'Montrose Selection'.

In side-by-side comparisons in Scottdale, Pa., under commercial practice, plants of the new Heucherella are different from plants of the female parent, the Heuchera sp. cultivar 'Quilter's Joy' in the following characteristics:

1. Leaves of plants of the new Heucherella have a striking metallic sheen that is not present on leaves of plants of the cultivar 'Quilter's Joy'.

2. Plants of the new Heucherella are more floriferous than plants of the cultivar 'Quilter's Joy'.

3. Flowering habit of plants of the new Heucherella is more uniform and the proportion of flowers to foliage is more aesthetically pleasing on plants of the new Heucherella compared to plants of the cultivar 'Quilter's Joy'.

4. Flowers of plants of the new Heucherella are showier and more attractive than flowers of plants of the cultivar 'Quilter's Joy'.

5. Plants of the new Heucherella flower for a longer period of time than plants of the cultivar 'Quilter's Joy'.

The following traits have been repeatedly observed and are determined to be the unique characteristics of 'Quicksilver'. These characteristics in combination distinguish the new Heucherella plant as a new and distinct cultivar:

1. Proportional plants with respect to quantity of flowers to foliage density.

2. Unique bronze leaves with a silver metallic sheen most pronounced in the interveinal areas. The bronze ground color varies with the season from purple-brown in the winter and spring to green-bronze in the summer. Silvery metallic sheen most pronounced autumn through spring.

3. Pink flower buds.

4. Numerous fringed, bell-shaped white flowers contrasted by dark flowering stems.

5. Excellent garden performance.

The new Heucherella plant has not been observed under all possible environmental conditions. The phenotype may vary significantly with variations in environment such as temperature, light level, nutrition and water status without, however, any variance in genotype.

Plants of the new Heucherella can be compared to plants of the commercial Heucherella cultivar 'Bridget Bloom' (not patented). In side-by-side comparisons in Scottdale, Pa., under commercial practice, plants of the new Heucherella are different from plants of the cultivar 'Bridget Bloom' in the following characteristics:

1. Inflorescences of plants of the new Heucherella are more floriferous, better proportioned and showier than inflorescences of plants of the cultivar 'Bridget Bloom'.

2. Plants of the new Heucherella flower for a longer period of time than plants of the cultivar 'Bridget Bloom'.

3. Plants of the new Heucherella are more vigorous than plants of the cultivar 'Bridget Bloom'.

4. Leaves of plants of the new Heucherella are metallic bronze and silver whereas leaves of plants of the cultivar 'Bridget Bloom' are green and maroon.

Plants of the new Heucherella can be compared to plants of the nonpatented Heucherella commercial cultivar 'Silver Streak'. In side-by-side comparisons in Scottdale, Pa., under commercial practice, plants of the new Heucherella are different from plants of the cultivar 'Silver Streak' in the following characteristics:

1. Inflorescences of plants of the new Heucherella are more floriferous, more compact, better proportioned and showier than inflorescences of plants of the cultivar 'Silver Streak'.

2. Plants of the new Heucherella flower for a longer period of time than plants of the cultivar 'Silver Streak'.

3. Plants of the new Heucherella are more vigorous than plants of the cultivar 'Silver Streak'.

4. Leaves of plants of the new Heucherella are metallic bronze and silver whereas leaves of plants of the cultivar 'Silver Streak' are bronze and gray.

BRIEF DESCRIPTION OF THE PHOTOGRAPHS

The accompanying colored photgraphs illustrate the overall appearance of the new cultivar, showing the colors as true as it is reasonably possible to obtain in colored reproductions of this type.

The photograph on the first sheet comprises a top perspective view of a nine-month plant of 'Quicksilver' during the summer.

The photograph on the second sheet comprises a close-up view of a typical flowering stem of 'Quicksilver'. Flower and foliage colors in the photographs may appear different from the actual colors due to light reflectance.

DETAILED BOTANICAL DESCRIPTION

The following observations, measurements, values, and comparisons describe plants grown in Scottdale, Pa., in a glass-covered greenhouse with day temperatures ranging from 16 to 27° C. and night temperatures ranging from 4 to 16° C. depending upon the season. In the following description, color references are made to The Royal Horticultural Society Colour Chart except where general terms of ordinary dictionary significance are used.

Classification:

*Botanical.*—×*Heucherella alba* cultivar 'Quicksilver'.

Parentage:

*Male or pollen parent.*—*Tiarella cordifolia* var. collina 'Montrose Selection' (not patented).

*Female or seed parent.*—Heuchera sp. cv. 'Quilter's Joy' (not patented).

Propagation:

*Type.*—By divisions, by shoot cuttings, or by tissue culture.

*Time to initiate roots.*—About 14 days at temperatures of 21° C.

*Time to develop roots.*—About 30 days at temperatures of 21° C.

*Rooting habit.*—Fibrous.

Plant description:

*Plant form and growth habit.*—Perennial, mounded foliage with numerous upright and strong flowering stems.

*Vigor.*—Vigorous, rapid growth rate.

*Crop time.*—From cuttings or rooted tissue-cultured plantlets, about nine months are required to produce mature flowering plants. Plants typically produced in 15-cm containers.

*Plant height, soil level to top of foliage.*—About 15 cm.

*Plant height, soil level to top of flowers.*—About 60 cm.

*Plant diameter.*—25 to 30 cm.

Foliage description:

*Arrangement.*—Rosette, single.

*Length.*—7 to 8 cm.

*Width.*—6 to 9 cm.

*Shape.*—Rounded cordate, 7-lobed.

*Apex.*—Broadly obtuse, lobed.

*Base.*—Cordate.

*Margin type.*—Crenate, ciliate.

*Venation pattern.*—Reticulate.

*Texture.*—Smooth, slightly rugose; slight pubescence on lower surface.

*Color.*—Unique bronze with a silver metallic sheen most pronounced in the interveinal areas. The bronze ground color varies with the season from purple-brown in the winter and spring to green-bronze in the summer. Silvery metallic sheet most pronounced autumn through spring. Young foliage, upper surface: 186D. Young foliage, lower surface: 187C. Mature foliage, upper surface: Autumn through spring, 186D; summer, 188B. Mature foliage, lower surface: Autumn through spring, 187C; summer, 186C. Venation, upper surface: Autumn through spring, 187A; summer, 189A underlain by black. Venation, lower surface: Same as leaf color.

*Petiole.*—Length: 5 to 9 cm. Diameter: 1 to 1.2 mm. Color: 186C.

*Durability of foliage to stress.*—Medium.

Flower description:

*Natural flowering season.*—Spring through summer, May until mid July in the Northern Hemisphere.

*Flower arrangement.*—Numerous single flowers arranged on airy and feathery panicles; usually about 60 to 70 flowers per flowering stem. Flowering continuous with numerous flowering stems forming throughout flowering period; usually about 8 to 10 flowering stems per plant.

*Flower appearance.*—Campanulate, persistent. Individual flowers last about one week on plant.

*Fragrance.*—None detected.

*Flower diameter.*—About 4.5 mm.

*Flower depth (height).*—About 6 mm.

*Flower bud.*—Length: About 3 mm. Diameter: About 2.5 mm. Shape: Bulbous. Color: 62D. Rate of opening: About 2 to 3 days.

*Petals.*—Appearance: Thin. Texture: Slightly pubescent. Arrangement: Radially symmetrical with five petals. Shape: Spatulate. Apex: Acute. Margin: Entire. Length: About 3 mm. Width: About 0.7 mm. Color: When opening, inner surface: White. When opening, outer surface: 62D. Fully opened, inner surface: White. Fully opened, outer surface: 62D, fading to white with subsequent development.

*Sepals/calyx.*—Appearance: Five sepals fused into a radially symmetrical calyx tube. Sepal apex: Obtuse. Sepal margin: Entire. Sepal texture: Thin, slightly pubescent. Sepal color: Inner surface: White. Outer surface: 62D. Calyx length: About 5 mm. Calyx diameter: About 6 mm.

*Peduncles.*—Angle: Erect. Strength: Strong. Color: 189A.

*Pedicels.*—Length: About 4 mm. Angle: Horizontal to drooping. Strength: Strong. Color. 189A underlain with black.

*Reproductive organs.*—Androecium: Stamen number: Five. Anther shape: Oval. Anther size: About 0.2 mm. Anther color: 157C. Amount of pollen: Moderate. Pollen color: 150D. Gynoecium: Pistil number: Two. Pistil length: About 5 mm. Stigma shape: Rounded. Stigma color: 157C. Style length: About 3.5 mm. Style color: 157C. Ovary color: 157C.

*Seed description.*—Plants are sterile and do not produce seed.

Disease resistance: Under commercial conditions, no resistance to diseases common to Heucherella have been observed.

It is claimed:

1. A new and distinct Heucherella plant named 'Quicksilver', as illustrated and described.

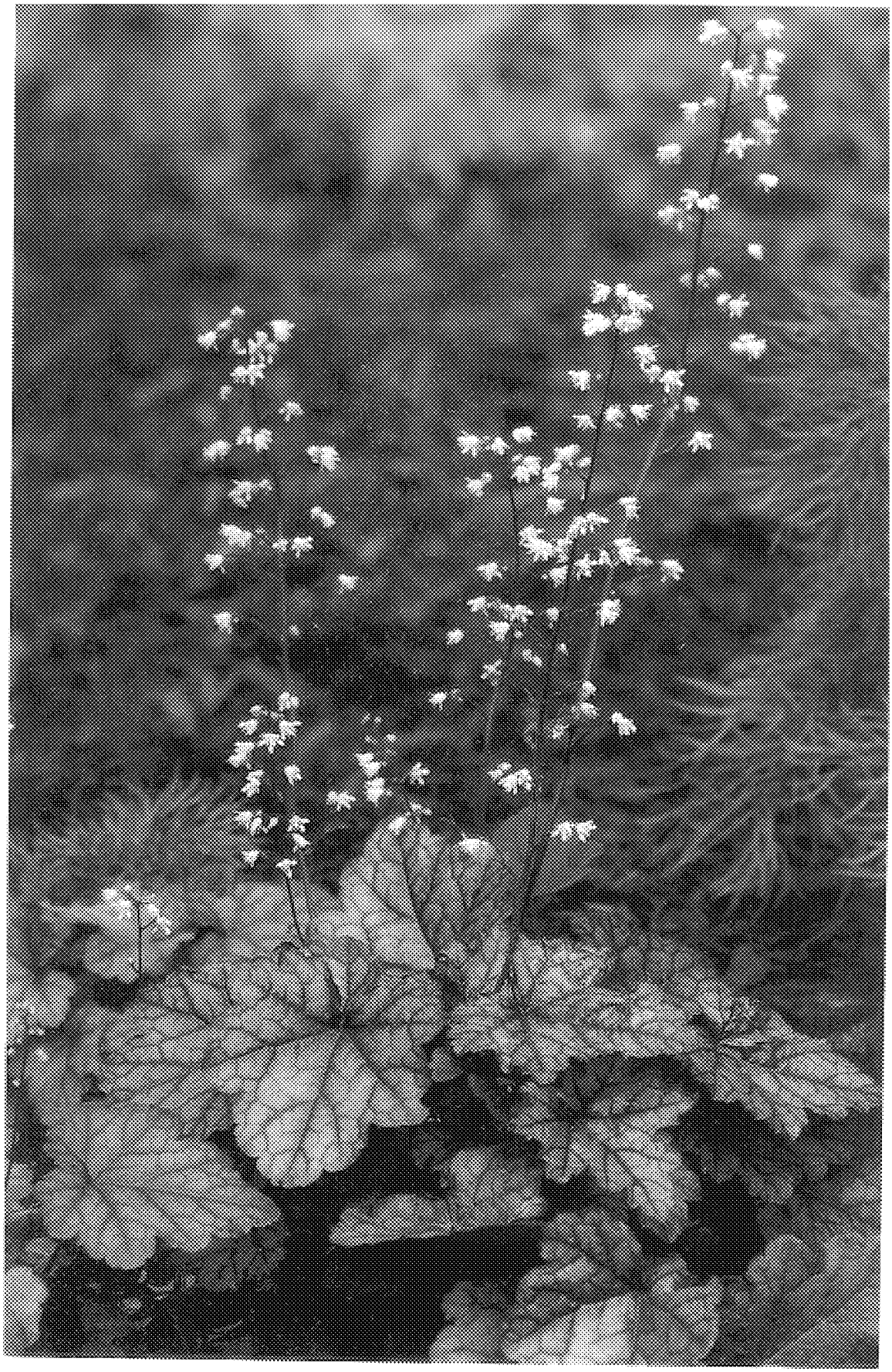

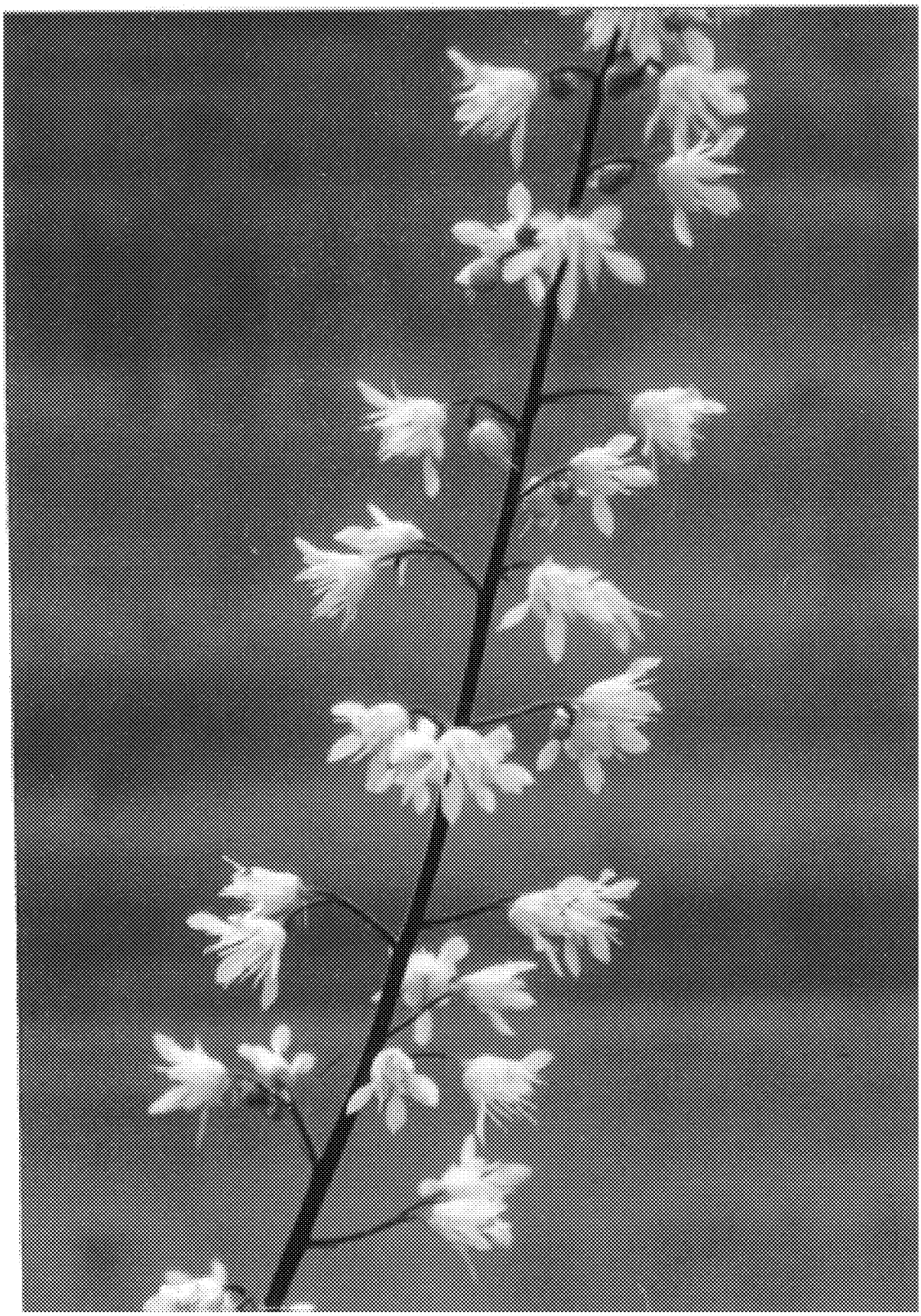

* * * * *